United States Patent
Park et al.

(10) Patent No.: US 11,730,658 B2
(45) Date of Patent: Aug. 22, 2023

(54) DEVICE FOR ASSISTING BODY MOVEMENT

(71) Applicant: NEOFECT CO., LTD., Seongnam-si (KR)

(72) Inventors: Byung Geol Park, Icheon-si (KR); Young Geun Choi, Yongin-si (KR); Seo Jeong Han, Seongnam-si (KR); Kyung Hwan Yoo, Incheon (KR)

(73) Assignee: NEOFECT CO., LTD., Seongnam-si (KR)

( * ) Notice: Subject to any disclaimer, the term of this patent is extended or adjusted under 35 U.S.C. 154(b) by 416 days.

(21) Appl. No.: 17/167,308

(22) Filed: Feb. 4, 2021

(65) Prior Publication Data
US 2021/0154082 A1   May 27, 2021

Related U.S. Application Data

(63) Continuation of application No. PCT/KR2019/009817, filed on Aug. 6, 2019.

(30) Foreign Application Priority Data

Aug. 9, 2018  (KR) .................. 10-2018-0093314
Aug. 6, 2019  (KR) .................. 10-2019-0095475

(51) Int. Cl.
*A61H 1/02*   (2006.01)

(52) U.S. Cl.
CPC ... *A61H 1/0288* (2013.01); *A61H 2201/0107* (2013.01); *A61H 2201/0176* (2013.01);
(Continued)

(58) Field of Classification Search
CPC ...... A61H 1/0274–0281; A61H 1/0285; A61H 1/0288; A61H 1/0237–0296;
(Continued)

(56) References Cited

U.S. PATENT DOCUMENTS 5,103,807 A * 4/1992 Makaran ............. A61H 1/0288
                                                        601/40
5,516,249 A * 5/1996 Brimhall ............. E02F 9/2008
                                                        703/3
(Continued)

FOREIGN PATENT DOCUMENTS

CN    105796283 A  *  7/2016   ........... A61H 1/0288
CN    105796283 A     7/2016
(Continued)

OTHER PUBLICATIONS

Translation of CN-107362000-A. Accessed from Espacenet May 12, 2023. (Year: 2017).*
(Continued)

*Primary Examiner* — Valerie L Woodward
*Assistant Examiner* — Paige Kathleen Bugg
(74) *Attorney, Agent, or Firm* — Studebaker & Brackett PC

(57) ABSTRACT

The present invention relates to a device for assisting body movement, comprising: a pulley for winding or unwinding a wire for moving a specific body between a first position and a second position; a motor for rotating the pulley forward or backward to wind the wire on or unwind the wire from the pulley; and a stopper portion for restricting winding or unwinding of the wire so that the specific body does not move out from between the first position and the second position, wherein the stopper portion comprises: a pulley hook that protrudes to form a swing trajectory on one side of the pulley; and a stopper formed to have a predetermined arc length along the swing trajectory of the pulley hook and provided with a stopper track to which the pulley hook is movably coupled.

11 Claims, 10 Drawing Sheets

(52) U.S. Cl.
CPC ............... *A61H 2201/1215* (2013.01); *A61H 2201/165* (2013.01); *A61H 2201/1635* (2013.01); *A61H 2201/1671* (2013.01)

(58) Field of Classification Search
CPC    A61H 2201/14–149; A61H 2201/1635–1638; A61H 2201/5053; A61H 2201/0176; A61H 2201/1215; A61H 2205/065–067; A61H 3/00–068; A61H 2003/001–065; A63B 21/124; B25J 9/0006
USPC ........................................................... 601/5
See application file for complete search history.

(56) References Cited

U.S. PATENT DOCUMENTS

| | | | | |
|---|---|---|---|---|
| 5,912,658 | A * | 6/1999 | Bergamasco | B25J 13/02 600/595 |
| 10,248,200 | B2 * | 4/2019 | Cohen | G06F 3/016 |
| 10,888,487 | B1 * | 1/2021 | Rogers | A41D 19/015 |
| 2017/0042704 | A1 * | 2/2017 | Ryu | A61F 2/583 |
| 2021/0161696 | A1 * | 6/2021 | Ewaldsson | A61H 1/0288 |
| 2021/0228430 | A1 * | 7/2021 | Farris | A61H 1/0244 |

FOREIGN PATENT DOCUMENTS

| | | | | |
|---|---|---|---|---|
| CN | 106913447 | A | | 7/2017 |
| CN | 107362000 | A * | 11/2017 | ............ A61H 1/0274 |
| CN | 107362000 | A | 11/2017 | |
| CN | 107374906 | A * | 11/2017 | ............ A61H 1/0218 |
| CN | 107432816 | A | 12/2017 | |
| CN | 107496139 | A * | 12/2017 | ............ A61B 5/1118 |
| DE | 102015007327 | A1 * | 8/2016 | |
| KR | 10-1163903 | B1 | 7/2012 | |
| KR | 10-2015-0121515 | A | 10/2015 | |
| KR | 10-2015-0138595 | A | 12/2015 | |
| WO | WO-9738759 | A1 * | 10/1997 | ............ A61F 5/0123 |
| WO | 2015/134336 | A2 | 9/2015 | |
| WO | 2017/187288 | A1 | 11/2017 | |
| WO | WO-2017187288 | A1 * | 11/2017 | ............ A61H 1/0288 |

OTHER PUBLICATIONS

Translation of DE-102015007327-A1. Accessed from Espacenet May 12, 2023. (Year: 2016).*
Translation of CN-107496139-A. Accessed from Espacenet May 12, 2023. (Year: 2017).*
Translation of CN-107374906-A. Accessed from Espacenet May 12, 2023. (Year: 2017).*
Translation of CN-105796283-A. Accessed from Espacenet May 12, 2023. (Year: 2016).*
Youtube video. This glove helps paralyzed hands move again Jan. 7, 2018, [retrieved on Oct. 29, 2019], Retrieved from the Internet: <URL: https://www.youtube.com/watch?v=9GAPfiwcsKI>.
International Search Report dated Nov. 13, 2019 for PCT/KR2019/009817.
The extended European search report issued by the European Patent Office dated May 3, 2022, which corresponds to European Patent Application No. 19846201.2-1122 and is related to U.S. Appl. No. 17/167,308.

* cited by examiner

DEVICE FOR ASSISTING BODY MOVEMENT

CROSS-REFERENCE TO RELATED APPLICATIONS

The present application is a continuation of International Patent Application No. PCT/KR2019/009817, filed on Aug. 6, 2019, which is based upon and claims the benefit of priority to Korean Patent Application Nos. 10-2018-0093314 filed on Aug. 9, 2018 and 10-2019-0095475 filed on Aug. 6, 2019. The disclosures of the above-listed applications are hereby incorporated by reference herein in their entirety.

BACKGROUND

Embodiments of the inventive concept described herein relate to a body movement assistance apparatus.

In general, joints of a human body have a structure in which body parts adjacent to the joints are rotatable about the joints.

Meanwhile, elderly people or rehabilitation patients with low muscular strength have difficulty in joint motion, compared to healthy people, and it is realistically difficult for the elderly people or the rehabilitation patients to do exercises with general exercise equipment even though they substantially require exercises.

In particular, in the case of a stroke or Parkinson's disease, various physical changes appear depending on states of the disease. Especially, these diseases are accompanied by phenomena in which hands are paralyzed and fingers are contracted.

If the paralysis of the hands and the contraction of the fingers are just left continually, muscles or joints become harder, and the patient may feel pain when moving and may have difficulty in normal activities even though nerves are restored.

Furthermore, elderly people or rehabilitation patients with low muscular strength have difficulty in joint motion, compared to healthy people, and it is realistically difficult for the elderly people or the rehabilitation patients to do exercises with general exercise equipment even though they substantially require exercises.

To enable patients incapable of moving joints normally to move the joints like normal people, an apparatus for assisting the patients in moving their joints is required.

SUMMARY

Embodiments of the inventive concept provide a body movement assistance apparatus for controlling a movement of a specific body part according to a degree to which a wire is wound or unwound, so as to enable a patient who is unable to freely move the specific body part due to lack of muscular strength of the specific body part or an abnormality in a nervous system to move the specific body part like a normal person.

Embodiments of the inventive concept provide a body movement assistance apparatus for preventing a wire from being excessively wound or unwound during a movement of a body part, so as to protect a patient, prevent an overload of a motor, and enable stable use.

According to an embodiment, a body movement assistance apparatus includes a pulley that winds or unwinds a wire for a movement of a specific body part between a first position and a second position, a motor that rotates the pulley in forward and reverse directions such that the wire is wound around or unwound from the pulley, and a stopper device that limits the winding or unwinding of the wire such that the specific body part does not deviate from between the first position and the second position. The stopper device includes a pulley hook protruding from one side of the pulley to form a turning trajectory and a stopper having a stopper track to which the pulley hook is movably coupled and that has a predetermined arc length along the turning trajectory of the pulley hook.

The body movement assistance apparatus may further include at least one disk that is provided between the pulley and the stopper so as to be rotatable and that adjusts a movement range of the specific body part between the first position and the second position. The disk may have a disk track having a predetermined arc length and corresponding to the turning trajectory of the pulley hook, and the disk may have, on a planar surface thereof, a disk hook formed at a position corresponding to the turning trajectory of the pulley hook.

The disk may include one disk. The pulley hook may be movably coupled to a disk track of the one disk, and a disk hook of the one disk may be movably coupled to the stopper track of the stopper.

The disk may include a plurality of disks. The pulley hook may be movably coupled to a disk track of a disk disposed to face the pulley among the plurality of disks. A disk hook of a disk disposed to face the stopper among the plurality of disks may be movably coupled to the stopper track. Each of the remaining disks may have a disk hook movably coupled to a disk track of an adjacent disk, and the remaining disks may be disposed in a row along a direction of a central axis of rotation of the pulley.

The body movement assistance apparatus may further include a battery that supplies power to the motor, and maximum operating time of the motor may be set to more than a period of time during which the motor is able to rotate in a state in which power of the battery is lowered.

The motor may be initially driven at a high output and may be driven at a gradually decreasing output as time passes.

When the motor rotates at a maximum output, the output of the motor may be reduced before the pulley hook movably coupled to the stopper track reaches one end portion of the stopper track.

In another embodiment, when the motor rotates at a maximum output, the output of the motor may be reduced before the disk hook of the disk movably coupled to the stopper track reaches one end portion of the stopper track.

The pulley and the motor may be detachably coupled.

The body movement assistance apparatus may further include a cover worn on the specific body part. The wire may include a first wire and a second wire that pull the cover. The first wire and the second wire may be disposed from a first point of the cover to a second point of the cover along an extension direction of the cover and may be disposed along at least part of a periphery of the cover in opposite directions at the second point of the cover.

One or more slits spaced apart from each other along the extension direction of the cover may be formed in an outer portion of the cover and an inner portion of the cover respectively. The one or more slits of the cover may be formed in a direction of knuckles of a body part received in the cover.

The first wire and the second wire may be disposed on an inner portion of the cover along the extension direction of the cover, may be disposed along the at least part of the periphery of the cover, and may be connected together on an outer portion of the cover.

BRIEF DESCRIPTION OF THE FIGURES

The above and other objects and features will become apparent from the following description with reference to the following figures, wherein like reference numerals refer to like parts throughout the various figures unless otherwise specified, and wherein:

FIG. 7 illustrates a state before the finger movement apparatus is worn;

FIG. 8 illustrates a state after the finger movement apparatus is worn;

DETAILED DESCRIPTION

The above and other aspects, features, and advantages of the inventive concept will become apparent from the following description of embodiments given in conjunction with the accompanying drawings. However, the inventive concept is not limited to the embodiments disclosed herein and may be implemented in various different forms. Herein, the embodiments are provided to provide complete disclosure of the inventive concept and to provide thorough understanding of the inventive concept to those skilled in the art to which the inventive concept pertains, and the scope of the inventive concept should be limited only by the accompanying claims and equivalents thereof.

Terms used herein are only for description of embodiments and are not intended to limit the inventive concept. As used herein, the singular forms are intended to include the plural forms as well, unless context clearly indicates otherwise. It will be further understood that the terms "comprise" and/or "comprising" specify the presence of stated features, components, and/or operations, but do not preclude the presence or addition of one or more other features, components, and/or operations. In addition, identical numerals will denote identical components throughout the specification, and the meaning of "and/or" includes each mentioned item and every combination of mentioned items. It will be understood that, although the terms first, second, etc. may be used herein to describe various components, these components should not be limited by these terms. These terms are only used to distinguish one component from another component. Thus, a first component discussed below could be termed a second component without departing from the teachings of the inventive concept.

Unless otherwise defined, all terms (including technical and scientific terms) used herein have the same meaning as commonly understood by those skilled in the art to which the inventive concept pertains. It will be further understood that terms, such as those defined in commonly used dictionaries, should not be interpreted in an idealized or overly formal sense unless expressly so defined herein.

Hereinafter, the inventive concept will be described in detail with reference to the accompanying drawings.

Prior to description, it should be noted that in this embodiment, a body movement assistance apparatus according to the inventive concept will be described as being applied to a finger, but the body movement assistance apparatus according to the inventive concept may be applied to a joint of a human body that has a rotatable structure.

Figure 1:
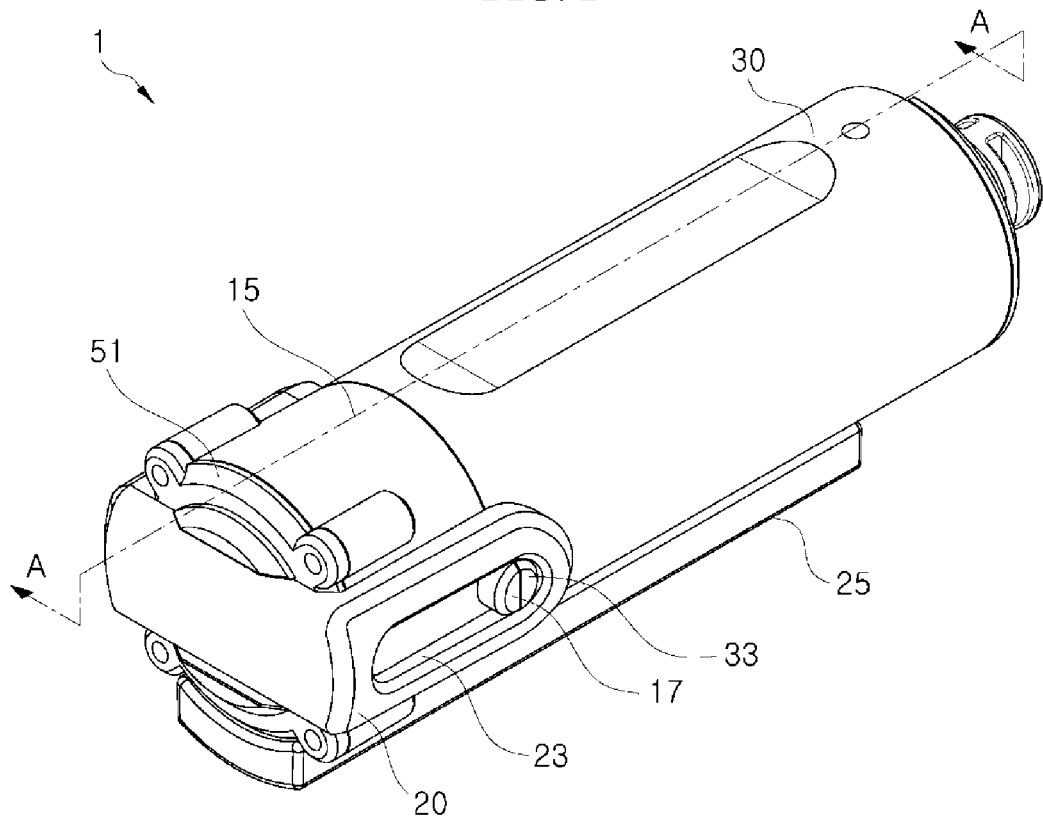
FIG. 1 is a perspective view of a body movement assistance apparatus according to an embodiment of the inventive concept.
Figure 3:
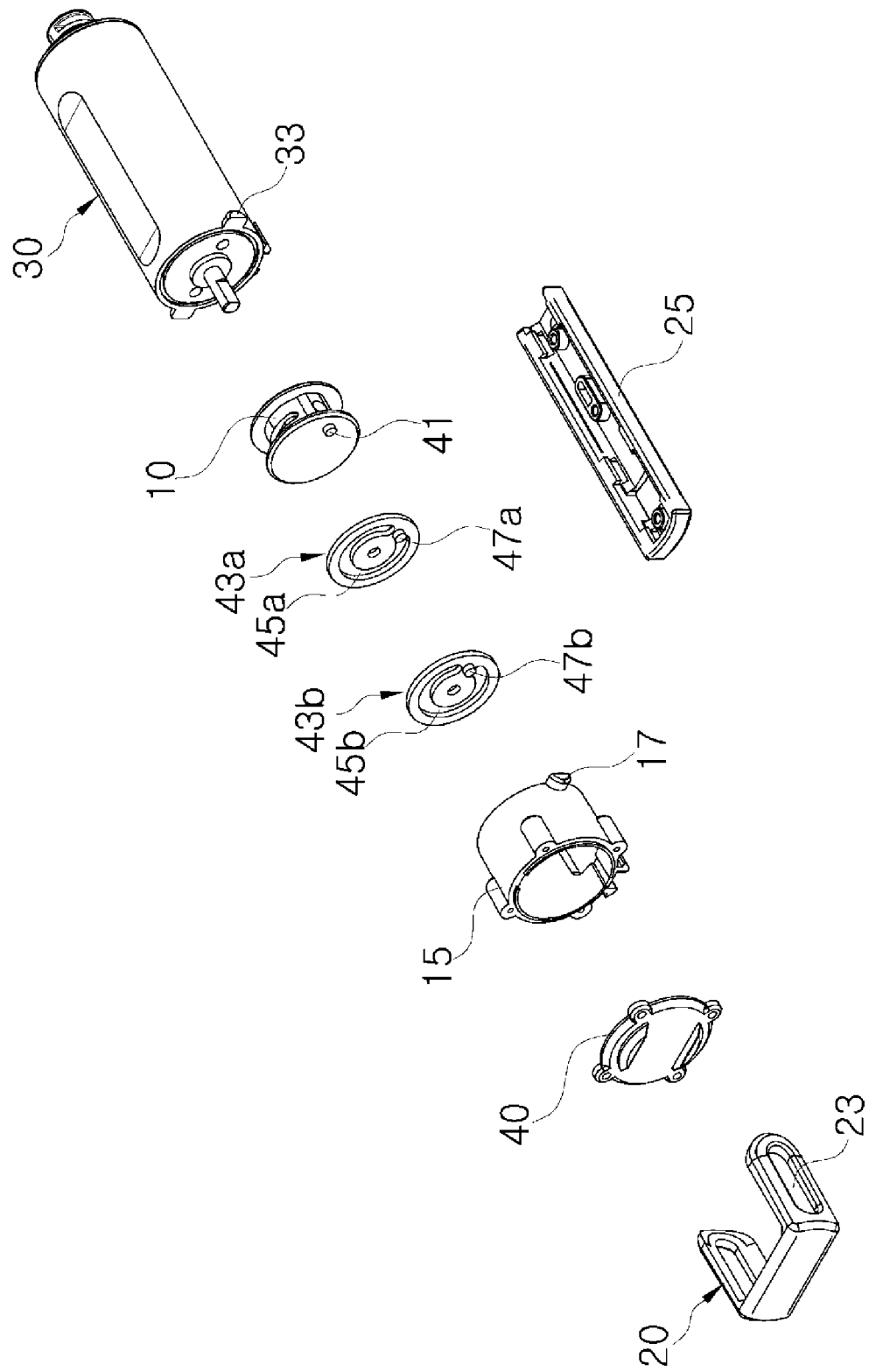
FIG. 3 is an exploded perspective view of the body movement assistance apparatus of FIG. 1.
Figure 4:
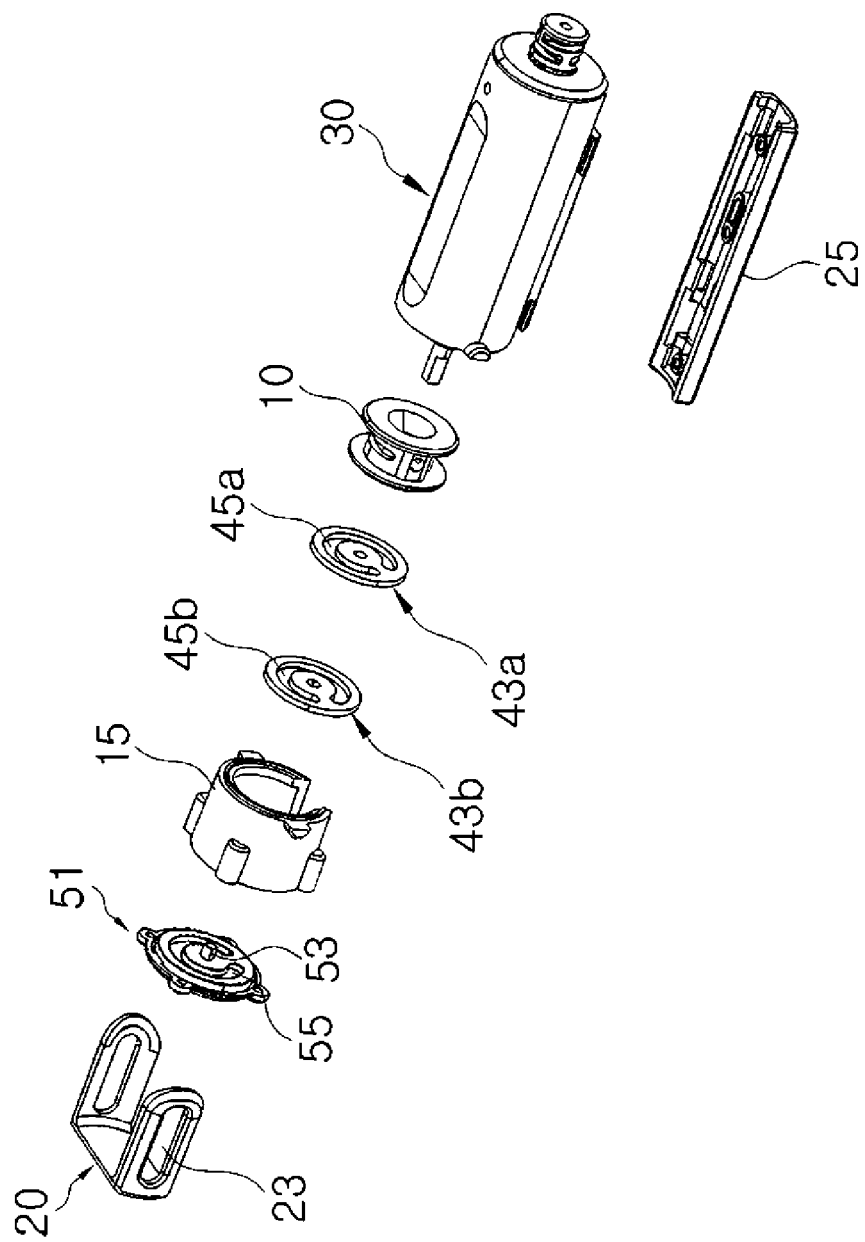
FIG. 4 is a rear exploded perspective view of the body movement assistance apparatus of FIG. 1.

FIG. 1 is a perspective view of a body movement assistance apparatus according to an embodiment of the inventive concept, and FIGS. 3 and 4 are exploded perspective views of the body movement assistance apparatus as viewed in different directions.

The body movement assistance apparatus 1 according to the embodiment of the inventive concept includes a pulley 10, a motor 30, and a stopper device.

A wire for moving a body part between a first position and a second position is wound around or unwound from the pulley 10.

The pulley 10 is rotatably received in a pulley housing 15 having a hollow cylindrical shape that is open at one side.

The pulley housing 15 has, on an outer circumferential surface thereof, housing coupling protrusions 17 detachably coupled to a bracket 20 for connecting the pulley housing 15 and the motor 30.

The bracket 20 has protrusion coupling holes 23 to which the housing coupling protrusions 17 are detachably coupled.

The motor 30 rotates the pulley 10, which is detachably coupled thereto, in forward and reverse directions. As the pulley 10 is rotated in the forward and reverse directions by the motor 30, the wire connected to the pulley 10 is wound around or unwound from the pulley 10.

The motor 30 is electrically connected with a battery and rotates by receiving power from the battery.

The motor 30 has, on an outer circumferential surface thereof, motor coupling protrusions 33 detachably coupled to the protrusion coupling holes 23 of the bracket 20.

The motor 30 and the pulley housing 15 are supported by a support 25 at the same time that the motor coupling protrusions 33 of the motor 30 and the housing coupling protrusions 17 of the pulley housing 15 are coupled to the protrusion coupling holes 23 of the bracket 20.

Accordingly, the motor 30 and the pulley housing 15 are coaxially coupled to form one drive module.

Figure 2:
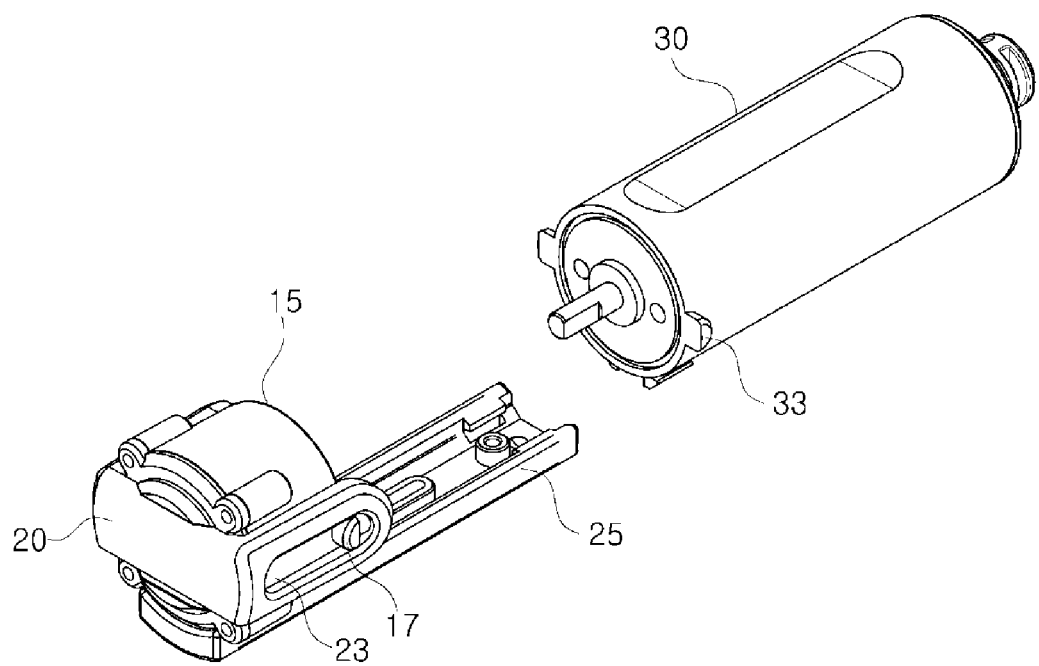
FIG. 2 is an exploded perspective view illustrating a pulley housing and a motor of FIG. 1.

As illustrated in FIG. 2, the motor 30 and the pulley housing 15 may be simply and conveniently separated from each other by separating the motor coupling protrusions 33 of the motor 30 from the protrusion coupling holes 23 of the bracket 20. Accordingly, the motor 30, the pulley 10, disks 43a and 43b to be described below, and the like may be replaced with products of different specifications depending on usage conditions, and maintenance thereof may be facilitated.

The stopper device limits winding or unwinding of the wire such that a specific body part does not deviate from between the first position and the second position.

The stopper device includes a pulley hook 41, the pair of disks 43a and 43b, and a stopper 51.

The pulley hook 41 has a predetermined diameter and protrudes to a predetermined height from one planar surface of the pulley 10 that faces toward the stopper 51. The pulley hook 41 rotates while forming a turning trajectory depending on the rotation of the pulley 10.

The pair of disks 43a and 43b have a disk shape with a predetermined thickness and are rotatable between the pulley 10 and the stopper 51. The disks 43a and 43b have disk tracks 45a and 45b having a predetermined arc length and corresponding to the turning trajectory of the pulley hook 41. Furthermore, the disks 43a and 43b have, on planar surfaces thereof, disk hooks 47a and 47b formed at positions corresponding to the turning trajectory of the pulley hook 41.

The pair of disks 43a and 43b may adjust a movement range of the specific body part between the first position and the second position according to a user's body movement condition. For example, the pair of disks 43a and 43b wind the wire around the pulley 10, or unwind the wire from the pulley 10, according to a movement distance of an index finger and a middle finger between the first position in which the index finger and the middle finger are spread apart and the second position in which the index finger and the middle finger are bent to grip a cup, for example, by adjusting the number of revolutions of the pulley 10 that corresponds to the sum of the arc lengths of the disk tracks 45a and 45b of the pair of disks 43a and 43b and the arc length of a stopper track 55.

Hereinafter, for convenience of description, the disk disposed to face the pulley 10 is referred to as the first disk 43a, and the disk disposed to face the stopper 51 is referred to as the second disk 43b.

The pair of disks 43a and 43b are received in the pulley housing 15 and are rotatably coupled to a stopper shaft 53 provided on a planar surface of the stopper 51 that faces toward the pulley 10.

The disk tracks 45a and 45b are formed in the planar surfaces of the pair of disks 43a and 43b to correspond to the turning trajectory of the pulley hook 41. The disk tracks 45a and 45b have an arc shape with a predetermined length. The disk tracks 45a and 45b of the pair of disks 43a and 43b have the same length. Alternatively, the disk tracks 45a and 45b of the pair of disks 43a and 43b may have different arc lengths.

The first disk hook 47a movably coupled to the second disk track 45b of the second disk 43b protrudes from the planar surface of the first disk 43a that faces toward the second disk 43b.

The second disk hook 47b movably coupled to the stopper track 55 of the stopper 51 to be described below protrudes from the planar surface of the second disk 43b that faces toward the stopper 51.

The pulley hook 41 is movably coupled to the first disk track 45a of the first disk 43a.

The stopper 51 has a disk shape with a predetermined thickness and is coupled to the pulley housing 15 to cover the open side of the pulley housing 15.

The stopper shaft 53, to which the pair of disks 43a and 43b are rotatably coupled, protrude to a predetermined height from the center of the planar surface of the stopper 51 that faces toward the second disk 43b.

On the planar surface of the stopper 51 that faces toward the second disk 43b, the stopper track 55 is formed around the stopper shaft 53. The stopper track 55 has an arc shape with a predetermined length, and the second disk hook 47b of the second disk 43b is movably coupled to the stopper track 55. The stopper track 55 is formed along a turning trajectory of the second disk hook 47b of the second disk 43b.

Figure 5:
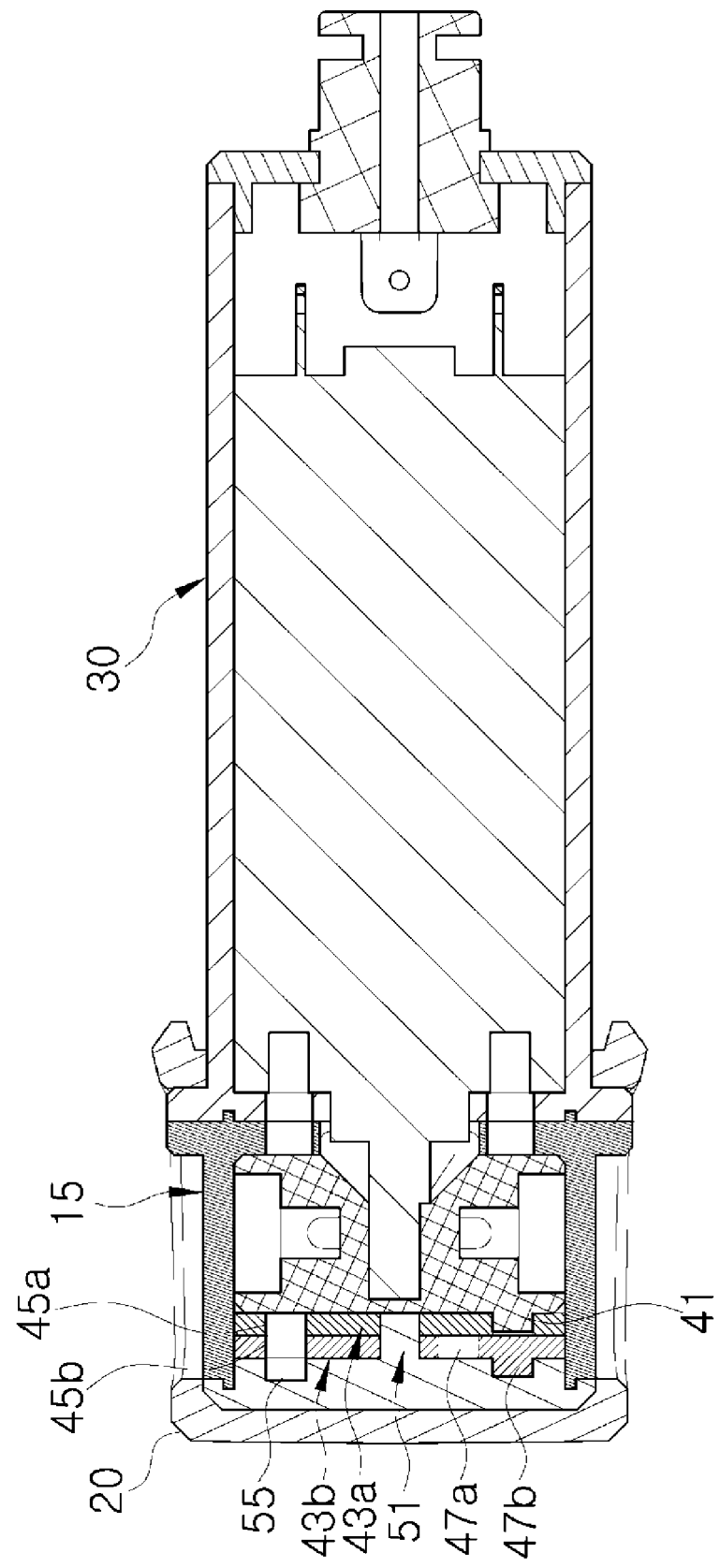
FIG. 5 is a sectional view taken along line A-A of FIG. 1.
Figure 6:
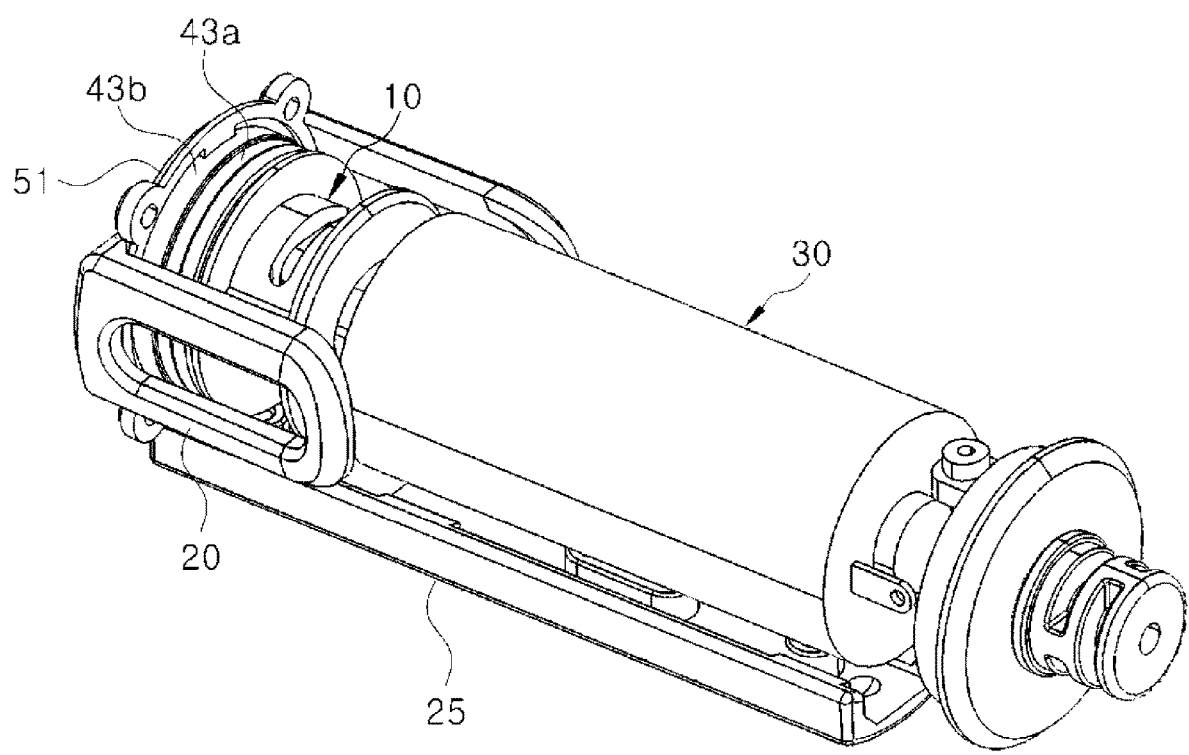
FIG. 6 is a view illustrating a state in which an upper area of FIG. 1 is partially cut away.

As illustrated in FIGS. 5 and 6, the pulley 10, the pair of disks 43a and 43b, and the stopper 51 are mutually connected in a row along the direction of the central axis of rotation of the pulley 10.

Although not illustrated, in another embodiment, the body movement assistance apparatus 1 according to the embodiment of the inventive concept may not include the pair of disks 43a and 43b, and the pulley hook 41 may be movably coupled to the stopper track 55 of the stopper 51 to limit winding or unwinding of the wire. In this case, the stopper track 55 of the stopper 51 is formed to correspond to a movement distance of the specific body part between the first position and the second position.

Although not illustrated, in another embodiment, one, three or more disks may be provided between the pulley 10 and the stopper 51. The number of disks may be adjusted according to the user's body movement condition, and the rotation of the pulley 10 may be adjusted such that the wire is wound around or unwound from the pulley 10.

For example, although not illustrated, when one disk is provided between the pulley 10 and the stopper 51, the pulley hook 41 may be movably coupled to a disk track of the disk, and a disk hook of the disk may be movably coupled to the stopper track 55 of the stopper 51.

Furthermore, when three or more disks are provided between the pulley 10 and the stopper 51, the remaining disks other than the disk disposed to face the pulley 10 and the disk disposed to face the stopper 51 may each have a disk hook movably coupled to a disk track of an adjacent disk, and the remaining disks may be disposed in a row along the direction of the central axis of rotation of the pulley 10.

Meanwhile, the body movement assistance apparatus 1 of the inventive concept may further include a remote controller.

The remote controller may include a power button, a grip button, and a release button. A wearer may press the power button to activate the remote controller and may press the grip button to perform a grip operation. In this case, the motor 30 may be rotated in the forward direction, and the wire may be pulled. Furthermore, the wearer may press the release button to perform a release operation. In this case, the motor 30 may be rotated in the reverse direction, and the wire may be released.

The remote controller may be worn on an arm of the wearer in a wearable form by a band. In this case, the remote controller may be attached to, or detached from, the band by a magnetic force. Furthermore, the remote controller may be wirelessly or wiredly connected with the motor 30. That is, a signal of the remote controller may be transferred to the motor 30 by wireless communication, or may be transferred to the motor 30 by an electric wire.

Hereinafter, a process of winding the wire around the pulley 10 to move the specific body part from the first position to the second position by using the above-configured body movement assistance apparatus 1 according to the embodiment of the inventive concept will be described.

When the motor 30 is driven such that the wire is wound around the pulley 10 in the state in which the pulley 10, the pair of disks 43a and 43b, and the stopper 51 are mutually connected in a row and the pulley 10 and the motor 30 are mutually coupled by the bracket 20, the motor 30 rotates in the forward direction, and accordingly the pulley 10 rotates in the forward direction.

As the pulley 10 rotates in the forward direction, the pulley hook 41 moves from one side of the first disk track 45a along the first disk track 45a and is stopped by an opposite side of the first disk track 45a.

Subsequently, the first disk 43a is rotated in the forward direction by rotary power of the pulley 10, and the first disk hook 47a moves from one side of the second disk track 45b of the second disk 43b along the second disk track 45b and is stopped by an opposite side of the second disk track 45b.

Thereafter, the second disk 43b is rotated in the forward direction by the rotary power of the pulley 10, and the second disk hook 47b moves from one side of the stopper track 55 of the stopper 51 along the stopper track 55 and is stopped by an opposite side of the stopper track 55 so that the pulley 10 does not rotate in the forward direction any more.

Accordingly, the pulley 10 rotates in the forward direction by an angle corresponding to the sum of the arc lengths by which the hooks 41, 47a, and 47b move along the tracks 45a, 45b, and 55.

The pulley 10 rotates a predetermined number of revolutions in the forward direction, and the wire is wound around the pulley 10 by a length corresponding to the distances by which the hooks 41, 47a, and 47a move along the tracks 45a, 45b, and 55. The specific body part is moved from the first position to the second position.

A process of unwinding the wire from the pulley 10 to move the specific body part from the second position to the first position by using the body movement assistance apparatus 1 according to the embodiment of the inventive concept is opposite to the above-described process of winding the wire, and therefore a specific description thereabout will be omitted.

When moving the specific body part between the first position and the second position, the body movement assistance apparatus 1 according to the embodiment of the inventive concept may prevent an excessive force from being applied to the specific body part, as well as preventing the wire from being wound around the pulley 10 by more than a preset winding length or preventing the wire from being reversely wound around the pulley 10 after unwound from the pulley 10 by a preset unwinding length. Furthermore, as the body movement assistance apparatus 1 controls a movement of the specific body part using the pulley 10, the motor 30, and the stopper device, an encoder for sensing the number of revolutions of the motor 30 is not required.

Meanwhile, when the wire is wound around, or unwound from, the pulley 10 according to a movement of the specific body part between the first position and the second position, maximum operating time of the motor 30 may be set to more than a period of time during which the motor 30 is able to rotate in a state in which the power of the battery is lowered.

Accordingly, the motor 30 cannot operate for more than the maximum time, and thus the motor 30 may be prevented from being overloaded and may be prevented from being continually rotated by an abnormal operation.

Here, the maximum operating time of the motor 30 may be differently set depending on a condition of the motor 30 and a body part and a physical condition of the user.

The motor 30 may be initially driven at a high output and may be driven at a gradually decreasing output as time passes. Alternatively, when the motor 30 rotates at a maximum output, the output of the motor 30 may be reduced before the disk hook 47b reaches one end portion of the stopper track 55.

Accordingly, the disk hook 47b, which moves along the stopper track 55, may be prevented from being damaged by impact caused by collision of the disk hook 47b with the one end portion of the stopper track 55.

Here, the above-described control of the motor 30 may be performed through a non-illustrated controller.

Figure 7:
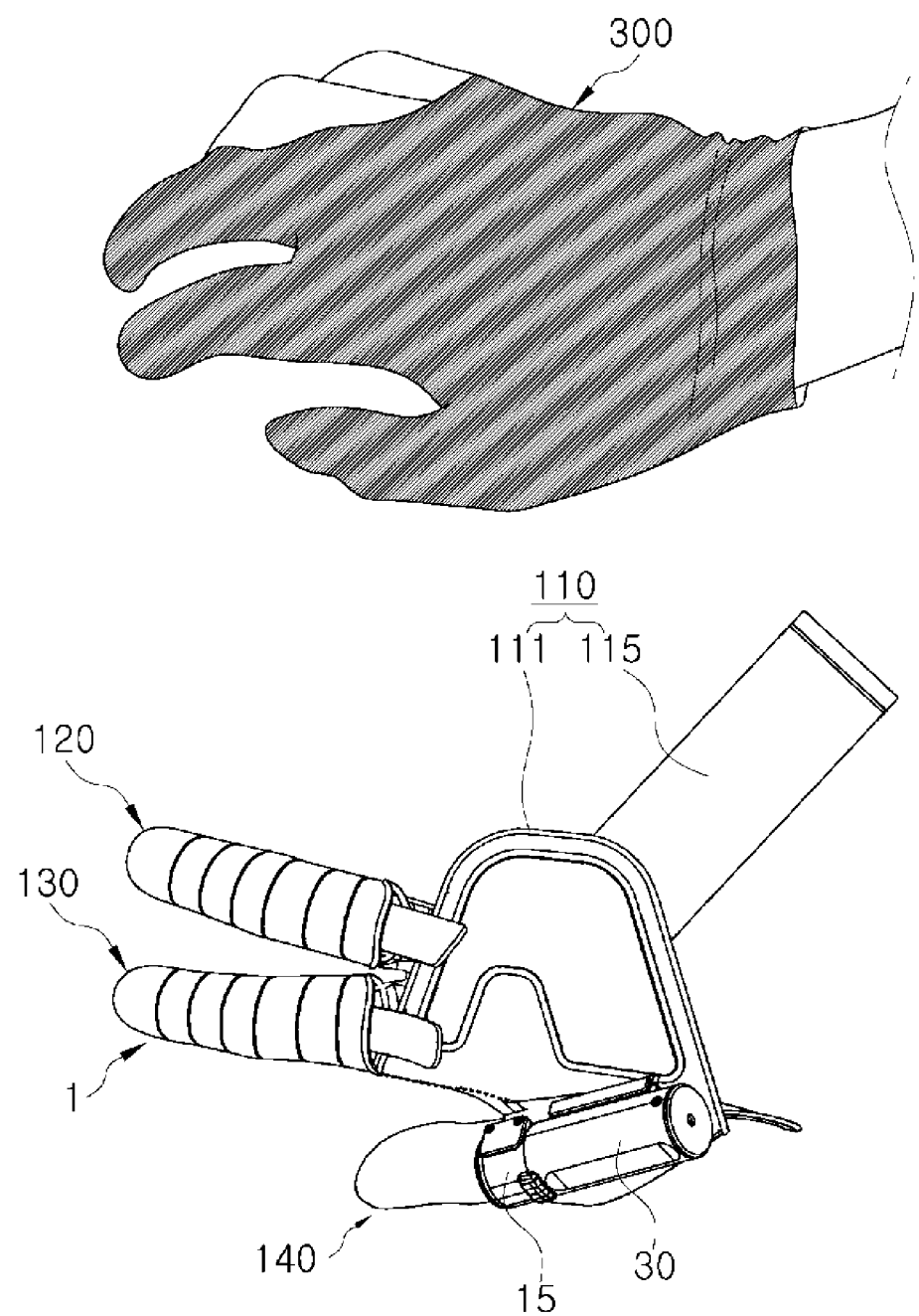
FIG. 7 is a view illustrating an embodiment in which the body movement assistance apparatus according to the embodiment of the inventive concept is applied to a finger movement apparatus, where

As illustrated in FIG. 7, the body movement assistance apparatus 1 according to the embodiment of the inventive concept may further include covers 120, 130, and 140 worn on specific body parts.

In this embodiment, it will be exemplified that the covers 120, 130, and 140 are worn on fingers that are examples of the specific body parts.

Hereinafter, prior to description, a side corresponding to the place where the palm of a wearer's hand is located is referred to as an "inside", and a side corresponding to the place where the back of the wearer's hand is located is referred to as an "outside"

Figure 10:
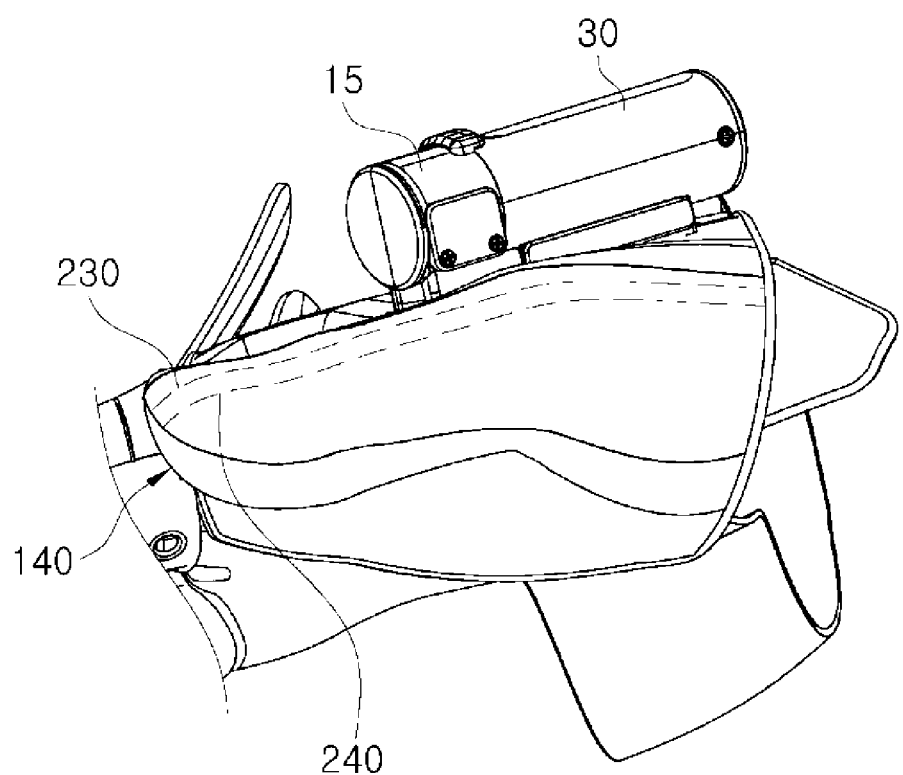
FIG. 10 is a view illustrating a state in which a first auxiliary strap and a second auxiliary strap are disposed in the finger movement apparatus of FIG. 8.

The body movement assistance apparatus 1 may assist in movements of index and middle fingers of the wearer by traction of wires by the motor and, as illustrated in FIG. 10, may fix the wearer's thumb using the rigidities of a first support strap 230 and a second support strap 240. In this case, the shape in which the thumb is bent and the degree to which the thumb is bent may be changed by deforming the first support strap 230 and the second support strap 240.

To effectively prevent slipping of the body movement assistance apparatus 1 in a state in which the wearer puts on an inner glove 300 as illustrated in FIG. 7, at least parts of a wearing part 110, the first cover 120, the second cover 130, and the third cover 140 may be formed of non-slip leather.

Figure 8:
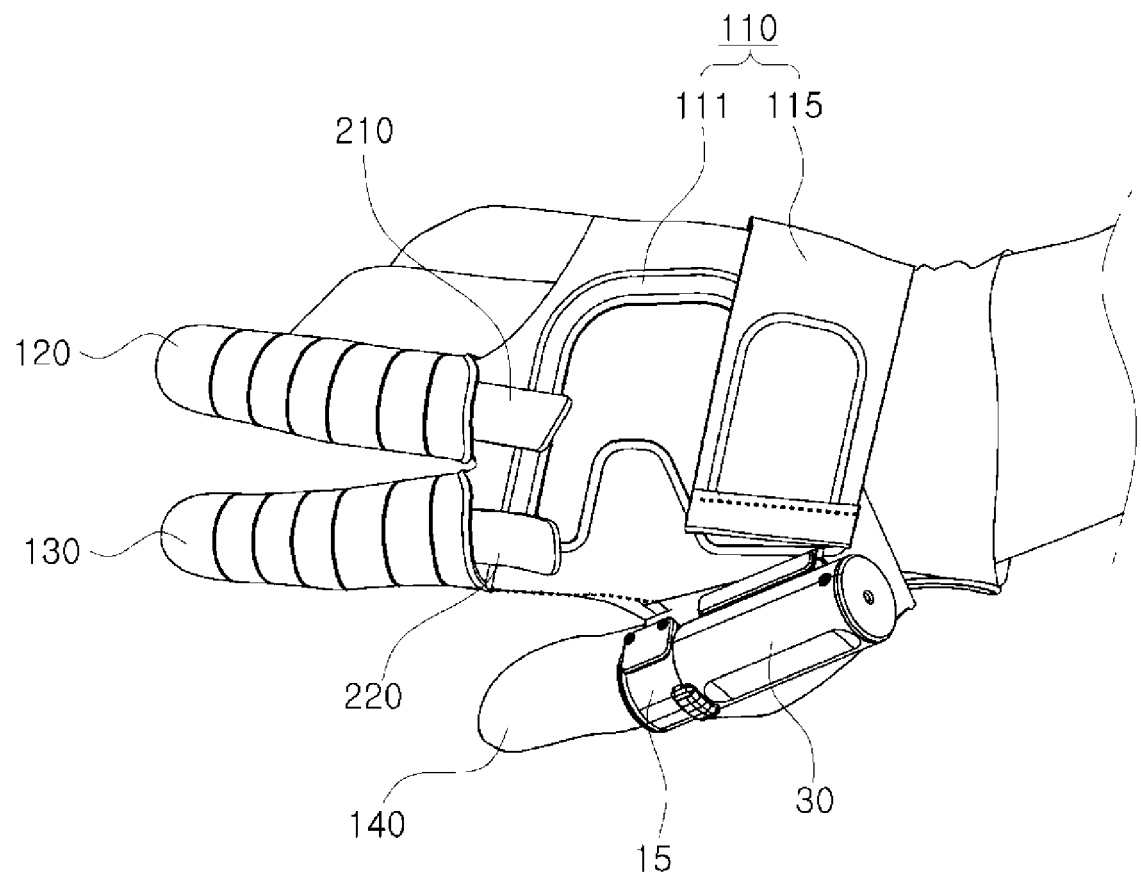
FIG. 8 is a view illustrating the embodiment in which the body movement assistance apparatus according to the embodiment of the inventive concept is applied to the finger movement apparatus, where
Figure 9:
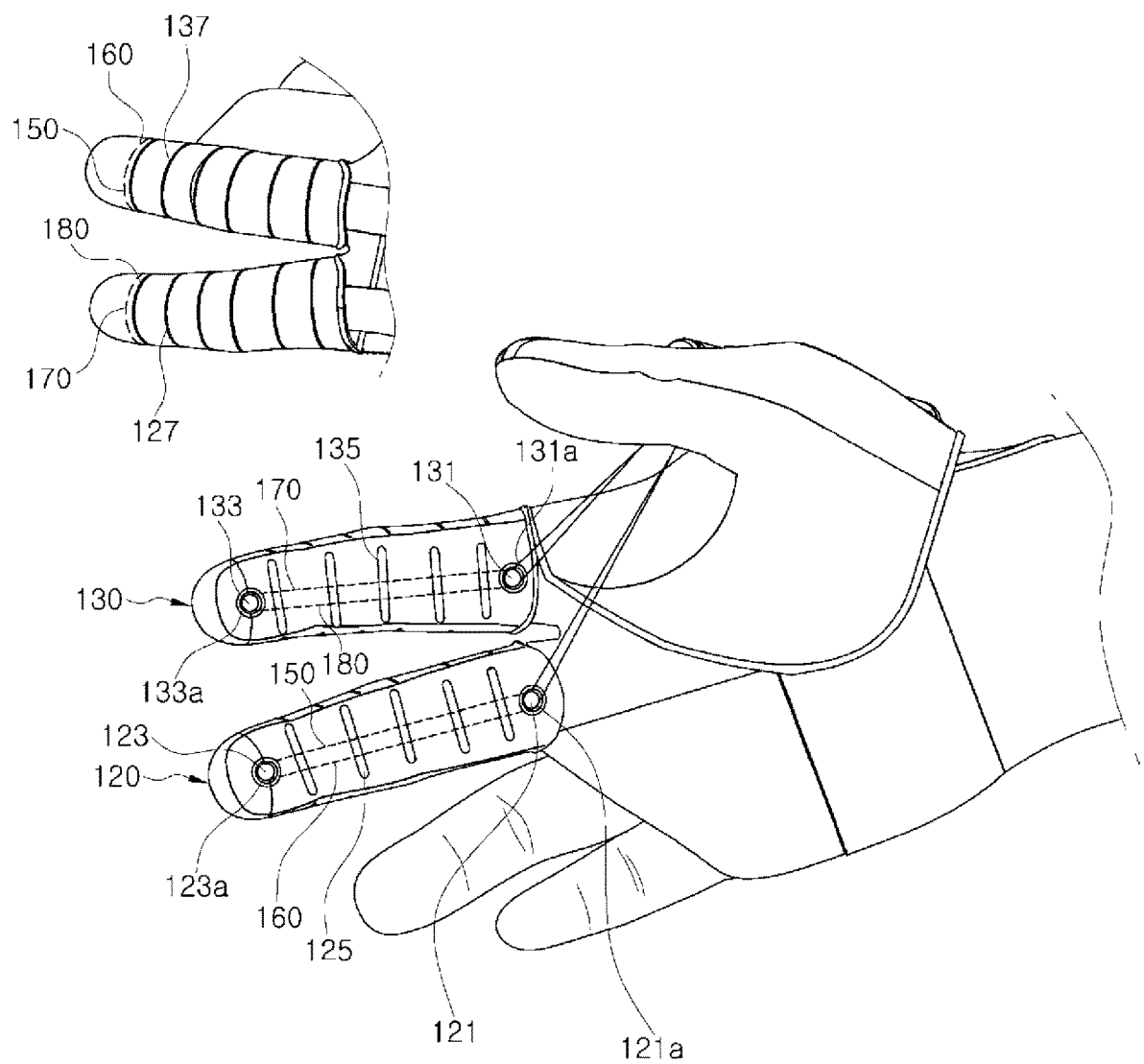
FIG. 9 is a view illustrating a state in which a first wire and a second wire are disposed in the finger movement apparatus of FIG. 8.

As illustrated in FIGS. 8 and 9, the body movement assistance apparatus 1 may further include the wearing part 110, the first cover 120, the second cover 130, the third cover 140, a first wire 150, a second wire 160, a third wire 170, a fourth wire 180, a first auxiliary strap 210, a second auxiliary strap 220, the first support strap 230, and the second support strap 240.

The wearing part 110 may surround at least part of the palm and back of the wearer's hand. The wearing part 110 may include a main body 111 having a Velcro formed or disposed on the outside thereof and a band 115 detachably coupled to the Velcro of the main body 111.

The first cover 120 may extend from the wearing part 110 in a first direction. The wearer's middle finger may be received in the first cover 120. The first cover 120 may be pulled and moved by the first wire 150 and the second wire 160. As a result, the first cover 120 may assist in a movement of the middle finger of the wearer.

A first point 121 and a second point 123 sequentially spaced apart from each other in the extension direction of the first cover 120 may be located on an inner portion of the first cover 120. A hole 121a in which a rivet is disposed may be formed at the first point 121 of the first cover 120, and a hole 123a in which a rivet is disposed may be formed at the second point 123 of the first cover 120.

The first cover 120 may have a plurality of slits 125 formed in the inner portion thereof. The plurality of slits 125 may be spaced apart from each other along the extension direction of the first cover 120. Furthermore, the first cover 120 may have a plurality of slits 127 formed in an outer portion thereof. The plurality of slits 127 may be spaced apart from each other along the extension direction of the first cover 120. The plurality of slits 125 formed in the inner portion of the first cover 120 and the plurality of slits 127 formed in the outer portion of the first cover 120 may be formed in the direction of knuckles of the middle finger received in the first cover 120. Natural bending of the actual finger may be implemented by the plurality of slits 125 formed in the inner portion of the first cover 120 and the plurality of slits 127 formed in the outer portion of the first cover 120.

The second cover 130 may extend from the wearing part 1 in a second direction. The wearer's index finger may be received in the second cover 130. The second cover 130 may be pulled and moved by the third wire 170 and the fourth wire 180. As a result, the second cover 130 may assist in a movement of the index finger of the wearer.

A first point 131 and a second point 133 sequentially spaced apart from each other in the extension direction of the second cover 130 may be located on an inner portion of the second cover 130. A hole 131a in which a rivet is disposed may be formed at the first point 131 of the second cover 130, and a hole 133a in which a rivet is disposed may be formed at the second point 133 of the second cover 130.

The second cover 130 may have a plurality of slits 135 formed in the inner portion thereof. The plurality of slits 135 may be spaced apart from each other along the extension direction of the second cover 130. Furthermore, the second cover 130 may have a plurality of slits 137 formed in an outer portion thereof. The plurality of slits 137 may be spaced apart from each other along the extension direction of the second cover 130. The plurality of slits 135 formed in the inner portion of the second cover 130 and the plurality of slits 137 formed in the outer portion of the second cover 130 may be formed in the direction of knuckles of the index finger received in the second cover 130. Natural bending of the actual finger may be implemented by the plurality of slits 135 formed in the inner portion of the second cover 130 and the plurality of slits 137 formed in the outer portion of the second cover 130.

The third cover 140 may extend from the wearing part 110 in a third direction. The wearer's thumb may be received in the third cover 140. The first support strap 230 and the second support strap 240 may be disposed inside the third cover 140. The third cover 140 may be fixed by the rigidities of the first support strap 230 and the second support strap 240. In addition, the shape of the third cover 140 may be modified depending on the shapes of the first support strap 230 and the second support strap 240. Accordingly, the materials of the first support strap 230 and the second support strap 240 may include a deformable rigid material. For example, the materials of the first support strap 230 and the second support strap 240 may include a flexible metallic material such as aluminum. The shape in which the thumb is bent and the degree to which the thumb is bent may be diversely implemented by deforming the shape of the third cover 140.

The first wire 150 and the second wire 160 may pull the first cover 120. The first wire 150 and the second wire 160 may be wound around the pulley 10.

The first wire 150 and the second wire 160 may be disposed from the first point 121 of the first cover 120 to the second point 123 of the first cover 120 along the extension direction of the first cover 120. Furthermore, the first wire 150 and the second wire 160 may be disposed along at least part of the periphery of the first cover 120 in opposite directions at the second point 123 of the first cover 120.

The first wire 150 and the second wire 160 may be disposed on the inner portion of the first cover 120 along the extension direction of the first cover 120. In this case, the first wire 150 and the second wire 160 may sequentially pass through the hole 121a located at the first point 121 of the first cover 120 and the hole 123a located at the second point 123 of the first cover 120.

The first wire 150 and the second wire 160 may be disposed along at least part of the periphery of the first cover 120 and may be connected together on the outer portion of the first cover 120. In this case, the first wire 150 and the second wire 160 may be connected together to form a single wire (may be integrally formed with each other). Furthermore, in this case, a receiving space for receiving the first wire 150 and the second wire 160 may be provided on the outer portion of the first cover 120.

As a result, when the pulley 10 received in the pulley housing 15 pulls the first wire 150 and the second wire 160, the first cover 120 may pull the middle finger to bend the middle finger. In this case, due to the above-described arrangement of the first wire 150 and the second wire 160, the first cover 120 may be bent inward at the same time that an outer distal end of the first cover 120 is pulled, thereby naturally assisting in a movement of the middle finger with high traction.

When the first wire 150 and the second wire 160 are connected together to form a single wire, the first wire 150 and the second wire 160 may be referred to as a "first cover wire".

That is, one end portion of the first cover wire 150 and 160 may be wound around the pulley 10. The first cover wire 150 and 160 may be withdrawn from the pulley 10, may extend from the first point 121 of the first cover 120 along the extension direction of the first cover 120, may be wound along at least part of the periphery of the first cover 120 at the second point 123 of the first cover 120, may return to the second point 123 of the first cover 120, and may extend to the first point 121 of the first cover 120 in the opposite direction to the extension direction of the first cover 120, and an opposite end portion of the first cover wire 150 and 160 may be wound around the pulley 10.

When the first cover wire 150 and 160 is wound along at least part of the periphery of the first cover 120, the first cover wire 150 and 160 may start from the inner portion of the first cover 120 and may return to the inner portion of the first cover 120 via the outer portion of the first cover 120.

The third wire 170 and the fourth wire 180 may pull the second cover 130. The third wire 170 and the fourth wire 180 may be wound around the pulley 10.

The third wire 170 and the fourth wire 180 may be disposed from the first point 131 of the second cover 130 to the second point 133 of the second cover 130 along the extension direction of the second cover 130. Furthermore, the third wire 170 and the fourth wire 180 may be disposed along at least part of the periphery of the second cover 130 in opposite directions at the second point 133 of the second cover 130.

The third wire 170 and the fourth wire 180 may be disposed on the inner portion of the second cover 130 along the extension direction of the second cover 130. In this case, the first wire 170 and the second wire 180 may sequentially pass through the hole 131a located at the first point 131 of the second cover 130 and the hole 133a located at the second point 133 of the second cover 130.

The third wire 170 and the fourth wire 180 may be disposed along at least part of the periphery of the second cover 130 and may be connected together on the outer portion of the second cover 130. In this case, the third wire 170 and the fourth wire 180 may be connected together to form a single wire. Furthermore, in this case, a receiving space for receiving the third wire 170 and the fourth wire 180 may be provided on the outer portion of the second cover 130.

As a result, when the third wire 170 and the fourth wire 180 are pulled, the second cover 130 may pull the index finger to bend the index finger. In this case, due to the above-described arrangement of the third wire 170 and the fourth wire 180, the second cover 130 may be bent inward at the same time that an outer distal end of the second cover 130 is pulled, thereby naturally assisting in a movement of the index finger with high traction.

When the third wire 170 and the fourth wire 180 are connected together to form a single wire, the third wire 170 and the fourth wire 180 may be referred to as a "second cover wire".

That is, one end portion of the second cover wire 170 and 180 may be wound around the pulley 10. The second cover wire 170 and 180 may be withdrawn from the pulley 10, may extend from the first point 131 of the second cover 130 along the extension direction of the second cover 130, may be wound along at least part of the periphery of the second cover 130 at the second point 133 of the second cover 130, may return to the second point 133 of the second cover 130, and may extend to the first point 131 of the second cover 130 in the opposite direction to the extension direction of the second cover 130, and an opposite end portion of the second cover wire 170 and 180 may be wound around the pulley 10.

When the second cover wire 170 and 180 is wound along at least part of the periphery of the second cover 130, the second cover wire 170 and 180 may start from the inner portion of the second cover 130 and may return to the inner portion of the second cover 130 via the outer portion of the second cover 130.

The first auxiliary strap 210 may extend from the wearing part 110 into the first cover 120. In this case, the first auxiliary strap 210 may be disposed inside the first cover 120. The first auxiliary strap 210 may be coupled with the outer portion of the first cover 120. Furthermore, a portion of the first auxiliary strap 210 exposed outside the first cover 120 may be detachably coupled to the Velcro of the main body 111 of the wearing part 110. The material of the first auxiliary strap 210 may include an elastic material having flexibility. For example, the material of the first auxiliary strap 210 may include Neopren.

The second auxiliary strap 220 may extend from the wearing part 110 into the second cover 130. In this case, the second auxiliary strap 220 may be disposed inside the second cover 130. The second auxiliary strap 220 may be coupled with the outer portion of the second cover 130. Furthermore, a portion of the second auxiliary strap 220 exposed outside the second cover 130 may be detachably coupled to the Velcro of the main body 111 of the wearing part 110. The material of the second auxiliary strap 220 may include an elastic material having flexibility. For example, the material of the second auxiliary strap 220 may include Neopren.

In summary, the first auxiliary strap 210 and the second auxiliary strap 220 may straighten the first cover 120 and the second cover 130 to implement stretch tension on the index and middle fingers of the wearer. In addition, the stretch tension on the wearer's index and middle fingers may be adjusted by changing the positions where the first auxiliary strap 210 and the second auxiliary strap 220 are attached to the Velcro of the main body 111 of the wearing part 110. As a result, the first auxiliary strap 210 and the second auxiliary strap 220 may adjust the stretch tension according to the degree of rigidity of the wearer's fingers to implement a neutral posture in design condition.

The first support strap 230 and the second support strap 240 may be disposed inside the third cover 140. The first support strap 230 and the second support strap 240 may be disposed adjacent to each other in the circumferential direction of the third cover 140. The first support strap 230 and the second support strap 240 may be disposed along the extension direction of the third cover 140.

The first support strap 230 and the second support strap 240 may have a flat plate shape. Furthermore, as described above, the materials of the first support strap 230 and the second support strap 240 may include a metallic material. For example, the materials of the first support strap 230 and the second support strap 240 may include an aluminum material. As a result, the first support strap 230 and the second support strap 240 may ensure rigidity greater than or equal to a predetermined level to fix the thumb of the wearer, and when a force greater than or equal to a predetermined level is applied, the first support strap 230 and the second support strap 240 may be deformed to implement the shape in which a thumb of a normal person is bent and the degree to which the thumb is bent.

Meanwhile, the pulley 10 and the motor 30 serve to wind or unwind the first wire 150, the second wire 160, the third wire 170, and the fourth wire 180.

The bracket 20 and the support 25 to which the pulley housing 15 and the motor 30 are coupled may be disposed on the main body 111 of the wearing part 110. In this case, the bracket 20 and the support 25 may be disposed between the second cover 130 and the third cover 140.

The first wire 150, the second wire 160, the third wire 170, and the fourth wire 180 are wound around the pulley 10 that is rotated by the motor 30. The first wire 150, the second wire 160, the third wire 170, and the fourth wire 180 may be pulled or released by being wound around or unwound from the pulley 10 by the rotation of the pulley 10.

Figure 11:
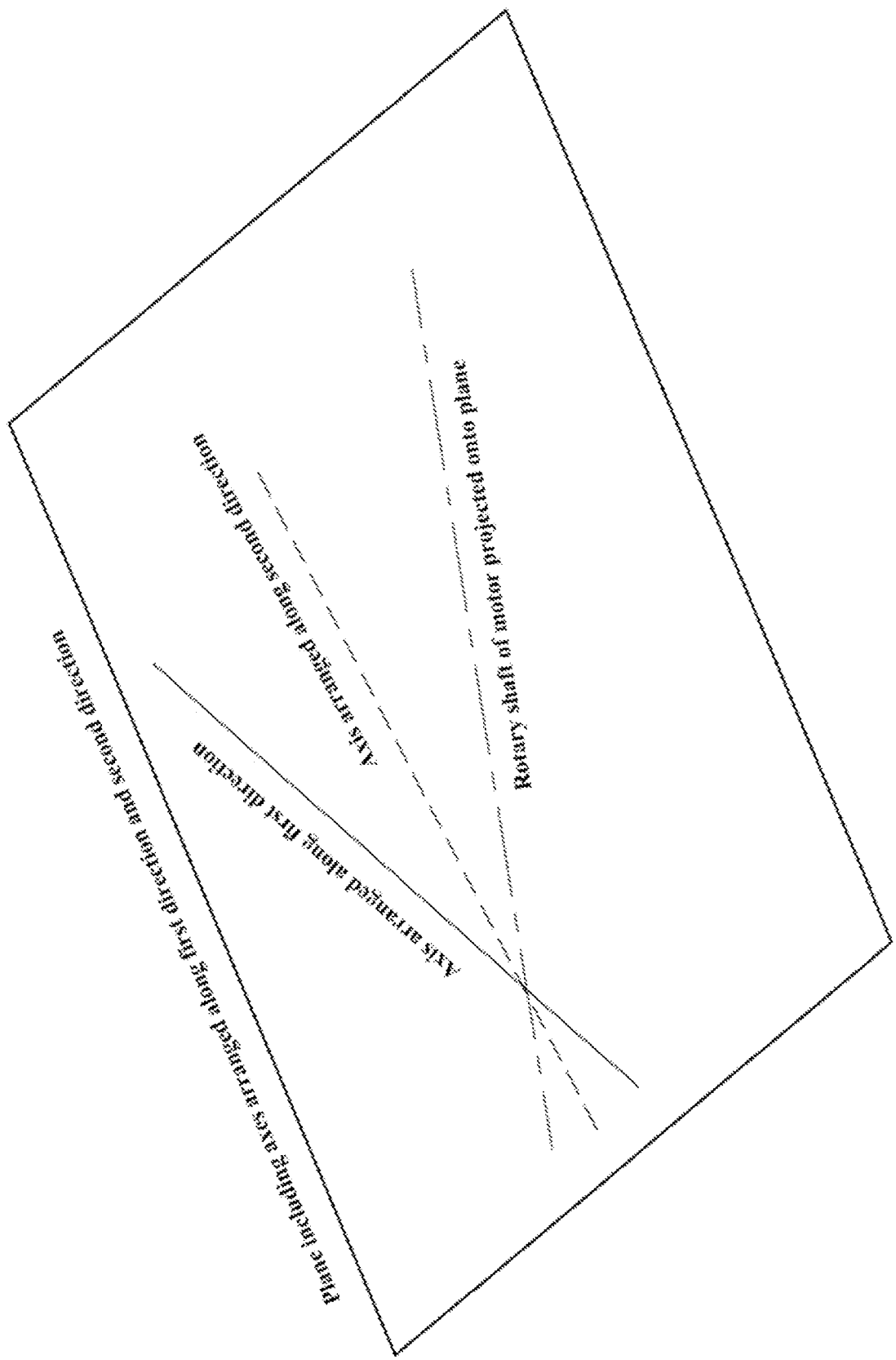
FIG. 11 is a schematic view illustrating that a rotary shaft of the motor of the inventive concept intersects an axis arranged along a first direction and an axis arranged along a second direction at one point.

As illustrated in FIG. 11, the rotary shaft of the motor 30 may form an acute angle with an axis arranged along the extension direction of the first cover 120 when projected onto a plane (e.g., a plane including the axis arranged along the extension direction of the first cover 120). In this case, the angle between the rotary shaft of the motor 30 and the axis arranged along the extension direction of the first cover 120 may range from 0 degrees to 80 degrees.

Likewise, the rotary shaft of the motor 30 may form an acute angle with an axis arranged along the extension direction of the second cover 130 when projected onto a plane (e.g., a plane including the axis arranged along the extension direction of the second cover 130). In this case, the angle between the rotary shaft of the motor 30 and the axis arranged along the extension direction of the second cover 130 may range from 0 degrees to 80 degrees.

Meanwhile, in the body movement assistance apparatus 1 of the inventive concept, the rotary shaft of the motor 30, when projected onto a plane including the axis arranged along the first direction (the extension direction of the first cover 120) and the axis arranged along the second direction (the extension direction of the second cover 130), may intersect the axis arranged along the first direction and the axis arranged along the second direction at approximately (substantially) one point.

That is, the rotary shaft of the motor 30 may intersect an extension line of the middle finger and an extension line of the index finger at the point where the extension line of the middle finger and the extension line of the index finger intersect each other. Accordingly, the first wire 150, the second wire 160, the third wire 170, and the fourth wire 180 may be prevented from being twisted. As a result, the first wire 150, the second wire 160, the third wire 170, and the fourth wire 180 may be continuously and stably pulled and released to implement accurate finger movement.

Hereinafter, a process of winding the first cover wire 150 and 160 and the second cover wire 170 and 180 around the pulley 10 to move the middle finger and the index finger from the first position to the second position by using the above-configured body movement assistance apparatus 1 according to the embodiment of the inventive concept will be described.

First, the first cover 120 and the second cover 130 are worn on the middle finger and the index finger, respectively.

Next, the bracket 20 and the support 25, to which the pulley housing 15 and the motor 30 are coupled, are fixed to the main body 111 of the wearing part 110.

Then, the motor 30 is driven in the forward direction such that the first cover wire 150 and 160 and the second cover wire 170 and 180 withdrawn from the first cover 120 and the second cover 130 and connected to the pulley 10 are wound around the pulley 10.

As the motor 30 rotates in the forward direction, the pulley 10 rotates in the forward direction, and the pulley hook 41 moves from the one side of the first disk track 45*a* along the first disk track 45*a* in the forward direction and is stopped by the opposite side of the first disk track 45*a*.

Subsequently, the first disk 43*a* is rotated in the forward direction by rotary power of the pulley 10, and the first disk hook 47*a* moves from the one side of the second disk track 45*b* of the second disk 43*b* along the second disk track 45*b* and is stopped by the opposite side of the second disk track 45*b*.

After that, the second disk 43*b* is rotated in the forward direction by the rotary power of the pulley 10, and the second disk hook 47*b* moves from the one side of the stopper track 55 of the stopper 51 along the stopper track 55 and is stopped by the opposite side of the stopper track 55 so that the pulley 10 does not rotate in the forward direction any more.

Accordingly, the pulley 10 rotates in the forward direction by an angle corresponding to the sum of the arc lengths by which the hooks 41, 47*a*, and 47*b* move along the tracks 45*a*, 45*b*, and 55.

The pulley 10 rotates a predetermined number of revolutions in the forward direction, and the first cover wire 150 and 160 and the second cover wire 170 and 180 are wound around the pulley 10 by a length corresponding to the distances by which the hooks 41, 47*a*, and 47*a* move along the tracks 45*a*, 45*b*, and 55. The middle finger and the index finger are moved from the first position in which the middle finger and the index finger are spaced apart from the thumb to the second position in which the middle finger and the index finger approach the thumb and grip an object located between the thumb and the middle and index fingers.

Accordingly, the body movement assistance apparatus 1 may be worn on a patient or an elderly person who has a finger disorder or is unable to grasp or hold an object due to a weak finger and may provide an auxiliary force for finger movement.

A process of unwinding the first cover wire 150 and 160 and the second cover wire 170 and 180 from the pulley 10 to move the middle finger and the index finger from the second position to the first position by using the body movement assistance apparatus 1 according to the embodiment of the inventive concept is opposite to the above-described process of winding the first cover wire 150 and 160 and the second cover wire 170 and 180, and therefore a specific description thereabout will be omitted As described above, the body movement assistance apparatus according to the inventive concept controls the movement of the specific body part according to the degree to which the wire is wound or unwound, thereby enabling the patient who is unable to freely move the specific body part due to lack of muscular strength of the specific body part or an abnormality in a nervous system to move the specific body part like a normal person. In addition, the body movement assistance apparatus prevents the wire from being excessively wound or unwound during the movement of the specific body part, thereby limiting an excessive movement of the specific body part, preventing an overload of the motor, and enabling stable use.

According the inventive concept, the body movement assistance apparatus controls the movement of the specific body part according to the degree to which the wire is wound or unwound, thereby enabling the patient who is unable to freely move the specific body part due to lack of muscular strength of the specific body part or an abnormality in a nervous system to move the specific body part like a normal person.

In addition, the body movement assistance apparatus prevents the wire from being excessively wound or unwound during the movement of the specific body part, thereby limiting an excessive movement of the specific body part, preventing the motor from being overloaded, and enabling stable use.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A body movement assistance apparatus comprising:
   a pulley configured to wind or unwind at least one wire for a movement of a specific body part between a first position and a second position;
   a motor configured to rotate the pulley in forward and reverse directions such that the at least one wire is wound around or unwound from the pulley; and
   a stopper device configured to limit the winding or unwinding of the at least one wire such that the specific body part does not deviate from between the first position and the second position,
   wherein the stopper device includes:
   a pulley hook protruding from one side of the pulley to form a turning trajectory;
   a stopper having a stopper track to which the pulley hook is movably coupled, the stopper track having a predetermined arc length along the turning trajectory of the pulley hook, and
   at least one disk provided between the pulley and the stopper so as to be rotatable and configured to adjust a movement range of the specific body part between the first position and the second position, wherein a first disk of the at least one disk comprises a disk track having a predetermined arc length and corresponding to the turning trajectory of the pulley hook,
   wherein the first disk has, on a planar surface thereof, a disk hook formed at a position corresponding to the turning trajectory of the pulley hook.

2. The body movement assistance apparatus of claim 1, wherein the pulley hook is movably coupled to the disk track of the first disk, and the disk hook of the first disk is movably coupled to the stopper track of the stopper.

3. The body movement assistance apparatus of claim 1, wherein the at least one disk includes a second disk, wherein the pulley hook is movably coupled to a disk track of the second disk disposed to face the pulley, wherein a disk hook of the first disk disposed to face the stopper is movably coupled to the stopper track, and wherein the disk hook of the second disk is movably coupled to the disk track of the first disk, and the first disk and the second disks are disposed in a row along a direction of a central axis of rotation of the pulley.

4. The body movement assistance apparatus of claim 1, further comprising:

a battery configured to supply power to the motor, wherein maximum operating time of the motor is set to more than a period of time during which the motor is able to rotate in a state in which power of the battery is lowered.

5. The body movement assistance apparatus of claim 1, wherein the motor is initially driven at a high output and is driven at a gradually decreasing output as time passes.

6. The body movement assistance apparatus of claim 1, wherein when the motor rotates at a maximum output, the output of the motor is reduced before the pulley hook movably coupled to the stopper track reaches one end portion of the stopper track.

7. The body movement assistance apparatus of claim 3, wherein when the motor rotates at a maximum output, the output of the motor is reduced before the disk hook of the first disk movably coupled to the stopper track reaches one end portion of the stopper track.

8. The body movement assistance apparatus of claim 1, wherein the pulley and the motor are detachably coupled.

9. The body movement assistance apparatus of claim 1, further comprising:

a cover configured to be worn on the specific body part, wherein the at least one wire includes a first wire and a second wire configured to pull the cover, and wherein the first wire and the second wire are disposed from a first point of the cover to a second point of the cover along an extension direction of the cover and are disposed along at least part of a periphery of the cover in opposite directions at the second point of the cover.

10. The body movement assistance apparatus of claim 9, wherein one or more slits spaced apart from each other along the extension direction of the cover are formed in an outer portion of the cover and an inner portion of the cover respectively, and wherein the one or more slits of the cover are configured to be formed in a direction of knuckles of a body part received in the cover.

11. The body movement assistance apparatus of claim 9, wherein the first wire and the second wire are disposed on an inner portion of the cover along the extension direction of the cover, are disposed along the at least part of the periphery of the cover, and are connected together on an outer portion of the cover.

* * * * *